(12) United States Patent
Okada et al.

(10) Patent No.: US 6,403,058 B1
(45) Date of Patent: Jun. 11, 2002

(54) PESTICIDAL AEROSOL FORMULATION

(75) Inventors: Kenya Okada, Takarazuka; Izumi Fujimoto, Minoo, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/376,729

(22) Filed: Aug. 17, 1999

(30) Foreign Application Priority Data

Sep. 28, 1998 (JP) .......................... 10-273087
Jan. 26, 1999 (JP) .......................... 11-016966

(51) Int. Cl.$^7$ ............................... A01N 25/06
(52) U.S. Cl. .................. 424/46; 424/45; 424/405; 424/421; 514/471
(58) Field of Search ............... 424/405, 45, 46, 424/421; 514/471, 149

(56) References Cited

U.S. PATENT DOCUMENTS

| | | | | |
|---|---|---|---|---|
| 3,081,223 A | * | 3/1963 | Gunning et al. | 424/46 |
| 3,124,505 A | * | 3/1964 | Doyle et al. | 424/46 |
| 4,597,895 A | * | 7/1986 | Bartlett | 424/46 |
| 4,742,060 A | | 5/1988 | Shiokawa et al. | 514/252 |
| 4,849,432 A | | 7/1989 | Shiokawa et al. | 514/341 |
| 5,034,404 A | | 7/1991 | Uneme et al. | 514/365 |
| 5,279,820 A | * | 1/1994 | Honda et al. | 424/78.08 |
| 5,304,566 A | | 4/1994 | Ishimitsu et al. | 514/357 |
| 5,346,699 A | * | 9/1994 | Tiernan et al. | 424/405 |
| 5,434,181 A | * | 7/1995 | Kodaka et al. | 514/471 |
| 5,532,365 A | | 7/1996 | Kodaka et al. | 544/212 |
| 5,750,548 A | | 5/1998 | Friedel et al. | 424/408 |

FOREIGN PATENT DOCUMENTS

| | | |
|---|---|---|
| AU | A20144/95 | 11/1995 |
| EP | 0428941 A1 | 5/1991 |
| JP | A6- 80505 | 3/1994 |

OTHER PUBLICATIONS

Dupont Freon: Aerosol Powders Aug. 1969.*

* cited by examiner

*Primary Examiner*—Neil S. Levy
(74) *Attorney, Agent, or Firm*—Birch, Stewart, Kolasch & Birch, LLP

(57) ABSTRACT

A pesticidal aerosol formulation which comprises (a) the compound shown by the general formula (1), (2) or (3) defined in the specification, (b) a powder carrier, (c) a propellant and (d) a solvent containing at least one selected from carboxylate esters being liquid at ordinary temperature and alcohols being liquid at ordinary temperature has an excellent efficiency for controlling pests especially termites.

8 Claims, No Drawings

PESTICIDAL AEROSOL FORMULATION

FIELD OF THE INVENTION

The present invention relates to a pesticidal aerosol formulation especially suitable for controlling termites.

BACKGROUND OF THE INVENTION

The houses damaged by termites have termite passages on or inside the surface of the wall, lumber, soil and so on. For controlling termites, especially for controlling the termites which inhabit the inside of the house, the method widely taken is that of pouring a controlling agent into the lumber or soil from the surface through a nozzle which is in a bored hole. However, in the application of a prior termite-controlling agent to houses, it was needed to pour the agent into many places for effective control in a wide area. Further, the applied agents are to penetrate into the wall of termite tunnels or a locus which termites inhabit, because said wall is wood in the case that the termite tunnel or the locus exists in the wood and said wall is soil solidified by termite secretion in the case that the termite tunnel or the locus exists in the soil. As a result, it is needed to pour a large amount of the agent to obtain a satisfactory controlling effect. Moreover, it is difficult to pour a large amount of agent into many places on walls or ceilings of houses, and so there are some cases that are difficult to apply the agent effectively.

The object of the present invention is to provide a pesticidal formulation suitable for termite-controlling having an excellent efficiency for controlling termites in houses.

SUMMARY OF THE INVENTION

The present inventors studied termite-controlling agents, and as a result, found that it is possible to control termites effectively even in the houses damaged by termites by using an aerosol formulation comprising a specific compound given in the general formula (1), (2) or (3), a powder carrier, a propellant and a specific solvent that is excellent in wide distribution at an application time and has decreased penetration into the wall of termite tunnels or lumber and completed the present invention.

In other words, the present invention serves a pesticidal aerosol formulation (hereinafter referred as to the present aerosol formulation) which comprises (a) a compound (hereinafter referred as to the present compound(s)) given by the general formula (1), (2) or (3):

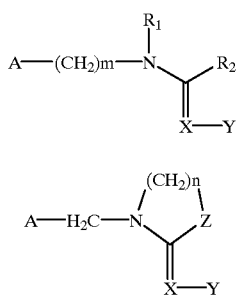

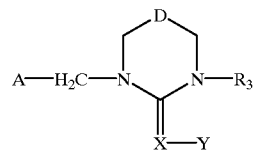

wherein A represents 6-chloro-3-pyridyl group, 2-chloro-5-thiazolyl group, tetrahydrofuran-2-yl group, tetrahydrofuran-3-yl group, 5-methyltetrahydrofuran-3-yl group, 3-pyridyl group, 6-bromo-3-pyridyl group, 3-cyanophenyl group, 2-methyl-5-thiazolyl group, 2-phenyl-5-thiazolyl group or 2-bromo-5-thiazolyl group; $R^1$ represents hydrogen atom, methyl group, ethyl group, formyl group or acetyl group; $R^2$ represents methyl group, amino group, methylamino group, N,N-dimethylamino group, ethylamino group, N,N-diethylamino group, N-methyl-N-ethylamino group, 1-pyrollidinyl group, (6-chloro-3-pyridyl)methylamino group or N-methyl-N-(6-chloro-3-pyridyl)methylamino group; $R^3$ represents methyl group, ethyl group, propyl group, propenyl group or propynyl group; X represents nitrogen atom or CH group; Y represents cyano group, nitro group or trifluoroacetyl group; Z represents NH group or sulfur atom; D represents oxygen atom or —N(CH$_3$)— group; m represents 0 or 1 and n represents 2 or 3, (b) a powder carrier, (c) a propellant and (d) a solvent containing at least one selected from carboxylate esters being liquid at room temperature and alcohols being liquid at ordinary temperature.

DETAILED DESCRIPTION OF THE INVENTION

The present compounds utilized in the present invention are known as an active ingredient for pesticides in U.S. Pat. No. 5,532,365, U.S. Pat. No. 4,742,060, U.S. Pat. No. 4,849,432, U.S. Pat. No. 5,034,404, U.S. Pat. No. 5,750,548, U.S. Pat. No. 5,304,566 and EP-428941A.

Examples of the compound of the general formula (1) in the present compounds include (E)-N$^1$-[(6-chloro-3-pyridyl)methyl]-N$^2$-cyano-N$^1$-methylacetamidine, N-[(6-chloro-3-pyridyl)methyl]-N-ethyl-N'-methyl-2-nitro-1,1-ethylidenediamine, 1-(6-chloro-3-pyridyl)methyl-3-methyl-2-cyanoguanidine, 1-(6-chloro-3-pyridyl)methyl-1,3-dimethyl-2-cyanoguanidine, 1-(6-chloro-3-pyridyl)methyl-1-ethyl-3-methyl-2-cyanoguanidine, 1-(6-chloro-3-pyridyl)methyl-1,3-dimethyl-3-(6-chloro-3-pyridyl)methyl-2-cyanoguanidine, 1-(6-chloro-3-pyridyl)methyl-3-methyl-2-nitroguanidine, 1-(6-chloro-3-pyridyl)methyl-3,3-dimethyl-2-nitroguanidine, 1-(6-chloro-3-pyridyl)methyl-1-methyl-2-nitroguanidine, 1-(6-chloro-3-pyridyl)methyl-1,3-dimethyl-2-nitroguanidine, 1-(6-chloro-3-pyridyl)methyl-3-ethyl-2-nitroguanidine, 1-(6-chloro-3-pyridyl)methyl-3-(6-chloro-3-pyridyl)methyl-2-nitroguanidine, 1-(6-chloro-3-pyridyl)methyl-3-methyl-2-trifluoroacetylguanidine, 1-(6-chloro-3-pyridyl)methyl-1-ethyl-3-methyl-2-nitroguanidine, 1-(6-chloro-3-pyridyl)methyl-1,3,3-trimethyl-2-nitroguanidine, 1-(6-chloro-3-pyridyl)methyl-2-nitroguanidine, 1-(6-chloro-3-pyridyl)methyl-1-ethyl-2-nitroguanidine, 1-(3-pyridyl)methyl-3-methyl-2-nitroguanidine, 1-(6-bromo-3-pyridyl)methyl-3-methyl-2-nitroguanidine, 1-(2-chloro-5-thiazolyl)methyl-3-methyl-2-nitroguanidine, 1-(3-cyanophenyl)-3-methyl-2-nitroguanidine, 1-(4-chlorophenyl)methyl-3-methyl-2-nitroguanidine, 1-(6- chloro-3-pyridyl)methyl-3, 3-dimethyl-1-formyl-2-nitroguanidine, 1-(6-chloro-3-pyridyl)methyl-3,3-dimethyl-1-acetyl-2-nitroguanidine, 1-(6-chloro-3-pyridyl)-3-methyl-2-cyanoguanidine, 1-(2-chloro-5-thiazolyl)methyl-3,3-dimethyl-2-nitroguanidine, 1-(2-chloro-5-thiazolyl)methyl-1-ethyl-3-methyl-2-nitroguanidine, 1-(2-chloro-5-thiazolyl)methyl-1-acetyl-3,3-dimethyl-2-nitroguanidine, 1-(6-chloro-3-pyridyl)methyl-1-methyl-2-trifluoroacetylguanidine, 1-(2-chloro-5-thiazolyl)methyl-1,3-dimethyl-2-nitroguanidine, 1-(2-chloro-5-thiazolyl)methyl-1-methyl-2-nitroguanidine, 1-(5-thiazolyl)methyl-3-methyl-2-nitroguanidine, 1-(2-methyl-5-thiazolyl)methyl-3,3-dimethyl-2-nitroguanidine, 1-(2-methyl-5-thiazolyl)methyl-3-methyl-2-nitroguanidine, 1-(2-phenyl-5-thiazolyl)methyl-3-methyl-2-nitroguanidine, 1-(2-chloro-5-thiazolyl)methyl-3,3-diethyl-2-nitroguanidine, 1-(2-chloro-5-thiazolyl)methyl-3-methyl-3-ethyl-2-nitroguanidine, 1-(2-chloro-5-thiazolyl)methyl-3-(1-pyrrolidinyl)-2-nitroguanidine, 1-(2-chloro-5-thiazolyl)methyl-1,3,3-trimethyl-2-nitroguanidine, 1-(2-bromo-5-thiazolyl)methyl-3-methyl-2-nitroguanidine, 1-(2-bromo-5-thiazolyl)methyl-3,3-dimethyl-2-nitroguanidine, 1-(2-chloro-5-thiazolyl)methyl-3-methyl-2-cyanoguanidine, 1-(tetrahydrofuran-3-yl)methyl-3-methyl-2-nitroguanidine and 1-(tetrahydrofuran-2-yl)methyl-3-methyl-2-nitroguanidine.

Examples of the compound of the general formula (2) in the present compounds include 3-[(6-chloro-3-pyridyl)methyl]-N-cyano-2-thiazolinimine and 1-[(6-chloro-3-pyridyl)methyl]-N-nitrotetrahydropyrimidin-2-imine.

Examples of the compound of the general formula (3) in the present compounds include 3-[(2-chloro-5-thiazolyl)methyl]-5-methyl-4-nitroiminotetrahydro-1,3,5-oxadiazine, 3,5-dimethyl-1-[(6-chloro-3-pyridyl)methyl]-2-nitroiminohexahydro-1,3,5-triazine, 3,5-dimethyl-1-[(2-chloro-5-thiazolyl)methyl]-2-nitroiminohexahydro-1,3,5-triazine, 3-ethyl-5-methyl-1-[(6-chloro-3-pyridyl)methyl]-2-nitroiminohexahydro-1,3,5-triazine, 3-n-propyl-5-methyl-1-[(6-chloro-3-pyridyl)methyl]-2-nitroiminohexahydro-1,3,5-triazine, 3-n-propyl-5-methyl-1-[(2-chloro-5-thiazolyl)methyl]-2-nitroiminohexahydro-1,3,5-triazine, 3-(2-propenyl)-5-methyl-1-[(6-chloro-3-pyridyl)methyl]-2-nitroiminohexahydro-1,3,5-triazine and 3-(2-propynyl)-5-methyl-1-[(6-chloro-3-pyridyl)methyl]-2-nitroiminohexahydro-1,3,5-triazine.

The amount of the present compound utilized in the present aerosol formulation is usually 0.0001 to 10% by weight.

Examples of the powder carrier utilized in the present invention include inorganic powders such as silicic acid compounds (for example, anhydrous silica), aluminum oxide, kaolin, talc, titanium oxide and magnesium carbonate; synthetic resin powders such as polyurethane, polyamide and polypropylene; and salts such as calcium stearate. It is preferable that the average diameter of the powder carrier is usually 50 μm or less and its shape is spherical or the like in the view of preventing choking of aerosol devise or leaking of gas. The amount of the powder carrier utilized in the present aerosol formulation is usually 1 to 20% by weight. The total amount of the present compound and the powder carrier is generally 1 to 30% by weight, preferably 5 to 15% by weight in the present aerosol formulation.

Examples of the propellant utilized in the present invention include liquefied gas such as liquefied petroleum gas, dimethyl ether and mixtures thereof. The amount utilized in the present aerosol formulation is usually 54 to 98% by weight.

Examples of the solvent utilized in the present invention include carboxylate esters being liquid at ordinary temperature such as isopropyl myristate, isopropyl palmitate, isopropyl decanoate and isopropyl laurate; alcohols being liquid at ordinary temperature such as ethanol and 2-propanol; and the mixtures of two or more said solvents. The carboxylate esters having a carbon number of 5 to 36, the alcohols having a carbon number of 1 to 5 and the mixtures thereof are preferable and isopropyl myristate, ethanol, 2-propanol and their mixtures are more preferable.

The ratio of the carboxylate esters being liquid at ordinary temperature and/or the alcohols being liquid at ordinary temperature in the solvent is usually 50% by weight or more, preferably 80% by weight or more and more preferably 90% by weight or more. The solvent essentially consisting of the carboxylate esters being liquid at ordinary temperature and/or the alcohols being liquid at ordinary temperature is particularly preferable. The amount of the solvent is usually 5 to 80 parts by weight, preferably 20 to 60 parts by weight in a practical situation and more preferably 30 to 50 parts by weight against 100 parts by weight of the total amount of the present compound and the powder carrier.

Additives, for example, stabilizers such as 2,6-di-t-butyl-4-methylphenol and 2,2'-methylenebis(4-methyl-6-t-butylphenol) and synergists such as N-(2-ethylhexyl)bicyclo[2.2.1]hept-5-ene-2,3-dicarboxyimide and 2-(2-butoxyethoxy)ethyl 6-propylpiperonyl ether may be added if necessary.

The present aerosol formulation is utilized for packing into aerosol container. Examples of the container include metallic containers such as iron container, zincked iron container, tin-plated iron container and aluminum container, resin-coated metallic container, for example, coated on the metal surface by epoxy resin, and so on.

Examples of the termites effectively controlled by the present aerosol formulation include Mastotermitidae, Termopsidae (Zootermopsis spp., Archotermopsis spp., Hodotermopsis spp., Porotermes spp., Stolotermes spp.), Kalotermitidae (Kalotermes spp., Neotermes spp., Cryptotermes spp., Incisitermes spp., Glyptotermes spp.), Hodotermitidae (Hodotermes spp., Microhodotermes spp., Anacanthotermes spp.), Rhinotermitidae (Reticulitermes spp., Heterotermes spp., Coptotermes spp., Schedolinotermes spp.), Serritermitidae and Termitidae (Amitermes spp., Drepanotermes spp., Hopitalitermes spp., Trinervitermes spp., Macrotermes spp., Odontotermes spp., Microtermes spp., Nasutitermes spp., Pericapritermes spp., Anoplotermes spp.).

Typical examples of the termites species objected in the present invention include *Recticulitermes speratus, Coptotermes formosanus, Incisitermes minor, Cryptotermes domesticus, Odontotermes formosanus, Neotermes koshunensis, Glyptotermes satsumensis, Glyptotermes nakajimai, Glyptotermes fuscus, Glyptotermeskodamai, Glyptotermes kushimensis, Hodotermopsis japonica, Coptotermes guangzhoensis, Reticulitermes miyatakei, Reticulitermes flaviceps amamianus*, Kanmonshiroari (Reticulitermes sp.), *Nasutitermes takasagoensis, Pericapritermes nitobei* and *Sinocapritermes mushae.*

The present aerosol formulation can contain one or more antimicrobial compound described below as well as the present compound and it can be possible to prevent the damage by fungi, bacteria and algae.

Examples of the antimicrobial compound include trihalophenyl compounds such as dichlorfluanid, trifluanid, folpet, fluorofolpet and so on; iodo compounds such IPBC, Amical 48 (produced by Abbott), IF1000 (produced by Nagase Sangyo), Sanplus (produced by Sankyo Co.) and so on; phenol compounds such as PCP-laurate, BDCP, tribromophenol and so on; azol compounds such as fenarimol, flurprimidol, fluotrimazol, triadimefon, triazimenol, diclobutrazol, paclobutrazol, diniconazole, uniconazole, triflumizole, flutriafol, flusilazole, penconazole, prochloraz, triarimol, fenarimol, bitertanol, imazalil, etaconazole, fenapanil, viniconazol, difenoconazole, bromoconazole, myclobutanil, hexaconazole, furconazole-cis, fenbuconazole, tebuconazole, propiconazole, azaconazole, cyproconazole and so on; carbamate compounds such as zineb, maneb, thiophanate-methyl, cypendazole, carbendazim, prothiocarb, diethofencarb and so on; antibiotics such as validamycin A, kasugamycin, milbemycin and so on; anilide compounds such as mepronil, flutolanil, pencycuron, carboxin, oxycarboxin, pyracarbolid, mebenil, furcarbanil, cyclafuramid, benodanil, metalaxyl, ofurace, benalaxyl, oxadixyl, cyprofuram, clozylacon, metsulfovax, tecloftalam and so on; organophosphorus compounds such as edifenphos, IBP, pyrazophos, aliette, tolclofos-methyl and so on; dicarboxyimide compounds such as dichlozoline, iprodione, vinclozolin, procymidone, myclozolin, fluoromide; tin compounds such as tributyltin octylate, tributyltin oleate, bis(tributyltin oxide), tributyltin naphthate, tributyltin phosphate, tributyltin benzoate and so on; thiocyanate compounds such as methylenebisthiocyanate, 2-thiocyanomethylthiobenzothiazole and so on; tertially ammonium compounds benzyl-dimethyl-tetradecyl ammonium chloride, benzyl-dimethyl-dodecyl ammonium chloride and so on; benzimidazole compounds such as fuberidazole, BCM, thiabendazole, benomyl and so on; isothiazolinone compounds; morpholine compounds such as tridemorph and so on; pyridine compounds; N-cyclohexyldiaziniumdioxy compounds; naphthenic acid compounds such as zinc naphthenate, copper naphthenate; quinoline compounds; boron compounds such as boric acid, borax, borate and so on; urea compounds; furan derivatives such as furmecyclox and so on.

Examples of the fungus prevented by the above-mentioned antimicrobial compounds include the fungus which change lumber color and the fungus which destroy lumber. The former include Ascomycetes such as Caratocystis spp. and so on; Deuteromycetes such as Aspergillus spp., Aureobasidium spp., Dactyleum spp., Penicillium spp., Aclerophoma spp., Scopularia spp., Tricoderma spp. and so on; Zygomycetes such as Mucor spp. and so on, and the latter include Ascomycetes such as Chaetomium spp., Humicola spp., Petriella spp., Trichurus spp. and so on; Basidiomycetes such as Coniophera spp., Coriolus spp., Donbiopora spp., Glenospora spp., Gloeophyllum spp., Len tin us spp., Paxillus spp., Pleurotus spp., Poria spp., Serpula spp., Tyromyces spp. and so on; Deuteromycetes such as Cladosporium spp. and so on.

The present aerosol formulation is prepared, for example, by packing the present compound, powder carrier and solvent, optionally the other additives into an aerosol container body, adding an aerosol valve to the aerosol container body and charging a propellant through the valve according to usual method.

The present aerosol formulation may be applied for forming an agent layer on the soil surface by spraying as a termite-controlling agent for soil treatment. However, it is better to be applied the present aerosol formulation to termite tunnel, lumber damaged by termites or locus where termites inhabit to obtain more effective result.

For the application to termite tunnel, a part of the termite tunnel is destroyed and the present aerosol formulation is applied inside the termite tunnel. Further, for the application to lumber damaged by termites or locus where termites inhabit, the present aerosol formulation is applied by pouring into the damaged lumber or termite-inhabiting locus if necessary holed. The amount of the application is usually about 0.00001 to 10000 mg per one place in an amount of the active ingredient and 1 to 20 g per one place in an amount of the present aerosol formulation except the propellant.

As described above, the present aerosol formulation can be utilized for controlling termites effectively. However, it can be utilized for controlling the other arthropod pests such as cockroaches, ants, millipeds, centipedes, sow bugs and so on as well as termites. In case that the present aerosol formulation is utilized for controlling those crawling pests, the application dosage is usually about 0.001 to 100 mg per $1m^2$ in an amount of the active ingredient.

EXAMPLES

Next, the present invention is explained by formulation examples and test examples in detail.

Formulation Example 1

A mixed powder of 0.005 g of (E)-$N^1$-[(6-chloro-3-pyridyl)methyl]-$N^2$-cyano-$N^1$-methylacetamidine (common name: acetamiprid) and 4.995 g of anhydrous silica, 1 g of isopropyl myristate and 1 g of 2-propanol are packed in an aerosol container, a valve is attached with the aerosol container and then 43 g of liquefied petroleum gas is charged into the aerosol container through the valve to afford an aerosol formulation.

Formulation Example 2

The same procedure as formulation example 1 except using 1-(tetrahydrofuran-3-yl)methyl-3-methyl-2-nitroguanidine in place of acetamiprid affords an aerosol formulation.

Formulation Example 3

The same procedure as formulation example 1 except using 3-[(2-chloro-5-thiazolyl)methyl]-5-methyl-4-nitroiminotetrahydro-1,3,5-oxadiazine in place of acetamiprid affords an aerosol formulation.

Reference Formulation Example 1

The same procedure as formulation example 1 except not using isopropyl myristate or 2-propanol and that an amount of utilized liquefied petroleum gas is 45 g affords an aerosol formulation.

Next, test examples are shown below.

Test Example 1

The aerosol formulation obtained by the formulation example 1 was sprayed on a plywood (15 cm×15 cm) from a distance of 10 cm in an amount of 0.1 g. A glass ring (4 cm in diameter, 2 cm in height) was put on the plywood and ten Formosan subterranean termites (*Coptotermes formosanus*) were released inside the glass ring. After 30 minutes, ten Formosan subterranean termites were gathered and transferred to a plastic petri dish (9 cm in diameter) where clean wet filter paper was spread on the bottom. The condition of the termites were observed at times. The same tests were performed utilizing the aerosol formulations obtained by the formulation example 2 and 3. The results are shown in table 1.

TABLE 1

| Tested Formulation | Percent Moribund after 1 day (%) |
|---|---|
| Formulation Example 1 | 100 |
| Formulation Example 2 | 87 |
| Formulation Example 3 | 100 |

Test Example 2

Each of the aerosol formulations obtained by the formulation example 1 and reference formulation example 1 was sprayed on a plywood (15 cm×15 cm) set vertically, from a distance of 10 cm in an amount of 0.1 g. The condition of liquid dripping and drying was observed. Non-dripping, quick drying and powdering after drying are desirable. The results are shown in table 2 below.

Evaluation

Dripping: None—A, Small—B, Large—C

Drying speed: Fast—A, Middle—B, Late—C

Powdering after drying: Much—A, Middle—B, Little—C

TABLE 2

| Tested Formulation | Liquid Dripping | Drying Speed | Powdering |
|---|---|---|---|
| Ref. Formulation Ex. 1 | C | B | A |
| Formulation Example 1 | A | A | A |

The present aerosol formulation is not only excellent in spreading character but also has low penetrating tendency into inner wall of termite way or lumber. As a result, for example, it can control termites effectively even in the houses damaged by termites.

What is claimed is:

1. A method for controlling termites which comprises applying an effective amount of the aerosol formulation which comprises (a) a compound known as 1-(tetrahydrofuran-3-yl) methyl-3-methyl-2-nitroguanidine, (b) a powder carrier, (c) a propellant and (d) a solvent containing at least one selected from carboxylate esters being liquid at room temperature and alcohols being liquid at room temperature to a termite tunnel, lumber damaged by termites or a locus termites inhabit.

2. The method according to claim 1, wherein the content of the compound (a) is 0.0001 to 10% by weight, the content of the powder carrier is 1 to 20% by weight, the content of the propellant is 54 to 98% by weight in the aerosol formulation and the amount of the solvent is 5 to 80 parts by weight against 100 parts by weight of the total amount of the present compound and the powder carrier.

3. The method according to claim 1, wherein the solvent contains 50% by weight or more of the solvents selected from carboxylate esters having 5 to 36 carbons and alcohols having 1 to 5 carbons.

4. The method according to claim 1, wherein the carboxylate ester is isopropyl myristate and the alcohol is ethanol or 2-propanol.

5. The method according to claim 1, wherein the solvent is isopropyl myristate, ethanol, 2-propanol or mixtures thereof.

6. The method according to claim 1, wherein the powder carrier is anhydrous silica.

7. The method according to claim 2, wherein the solvent is isopropyl myristate, ethanol, 2-propanol or mixtures thereof.

8. The method according to claim 7, wherein the powder carrier is anhydrous silica.

* * * * *